(12) United States Patent
Hyman et al.

(10) Patent No.: US 6,555,331 B1
(45) Date of Patent: Apr. 29, 2003

(54) BACTERIOPHAGE ASSAY

(75) Inventors: Lizbeth Jane Hyman, Dundee (GB); Ian Karoly Toth, Fife (GB)

(73) Assignee: Scottish Crop Research Institute, Dundee (GB)

( * ) Notice: Subject to any disclaimer, the term of this patent is extended or adjusted under 35 U.S.C. 154(b) by 0 days.

(21) Appl. No.: 09/674,537

(22) PCT Filed: Apr. 30, 1999

(86) PCT No.: PCT/GB99/01363

§ 371 (c)(1),
(2), (4) Date: Jan. 12, 2001

(87) PCT Pub. No.: WO99/57304

PCT Pub. Date: Nov. 11, 1999

(30) Foreign Application Priority Data

May 2, 1998 (GB) ............................................. 9809414

(51) Int. Cl.⁷ ............................ C12Q 1/00; C12Q 1/04; A61K 39/12; A01N 63/00
(52) U.S. Cl. ................................ 435/34; 435/4; 435/5; 435/7.1; 435/30; 424/204.1; 424/234.1; 424/93.3; 424/235.1
(58) Field of Search ........................... 435/4, 5, 7.1, 30, 435/34; 424/204.1, 234.1, 93.3, 235.1, 239

(56) References Cited

U.S. PATENT DOCUMENTS 4,591,567 A    5/1986   Britten et al. ............... 435/293
6,344,362 B1 * 2/2002   Fassina et al. .............. 436/501

FOREIGN PATENT DOCUMENTS

WO    90/04041    4/1990
WO    97/39111    10/1997

OTHER PUBLICATIONS

Biological Abstracts, vol. 75, Abstract No. 79944, XP002112991, "Psychrotropic bacteriophages for beef Spoilage pseudomonas", Journal of Food Proteins, vol. 45, No. 14, 1982, pp. 1318–1325.

* cited by examiner

Primary Examiner—James Housel
Assistant Examiner—Stacy S. Brown
(74) Attorney, Agent, or Firm—Drinker Biddle & Reath LLP

(57) ABSTRACT

There is provided an assay suitable for the typing of bacterial strains. In the assay a predetermined amount of phage is combined with a bacterial isolate of unknown strain, the mixture being located in a suitable container. The mixture of phage and bacteria is conveniently held in a liquid or semi-liquid medium facilitating interaction of the two species. The extent of bacterial growth in the presence of the phage is measured by conventional means, preferably by means of an OD reading. Desirably the phage is retained in the selected container, which is conveniently a micro-titer plate, through use of a fixant such as 5% gelatin.

16 Claims, 14 Drawing Sheets

↑ Light

Key

● Phage particle

◯ Bacterial cell

◁ Cell debris

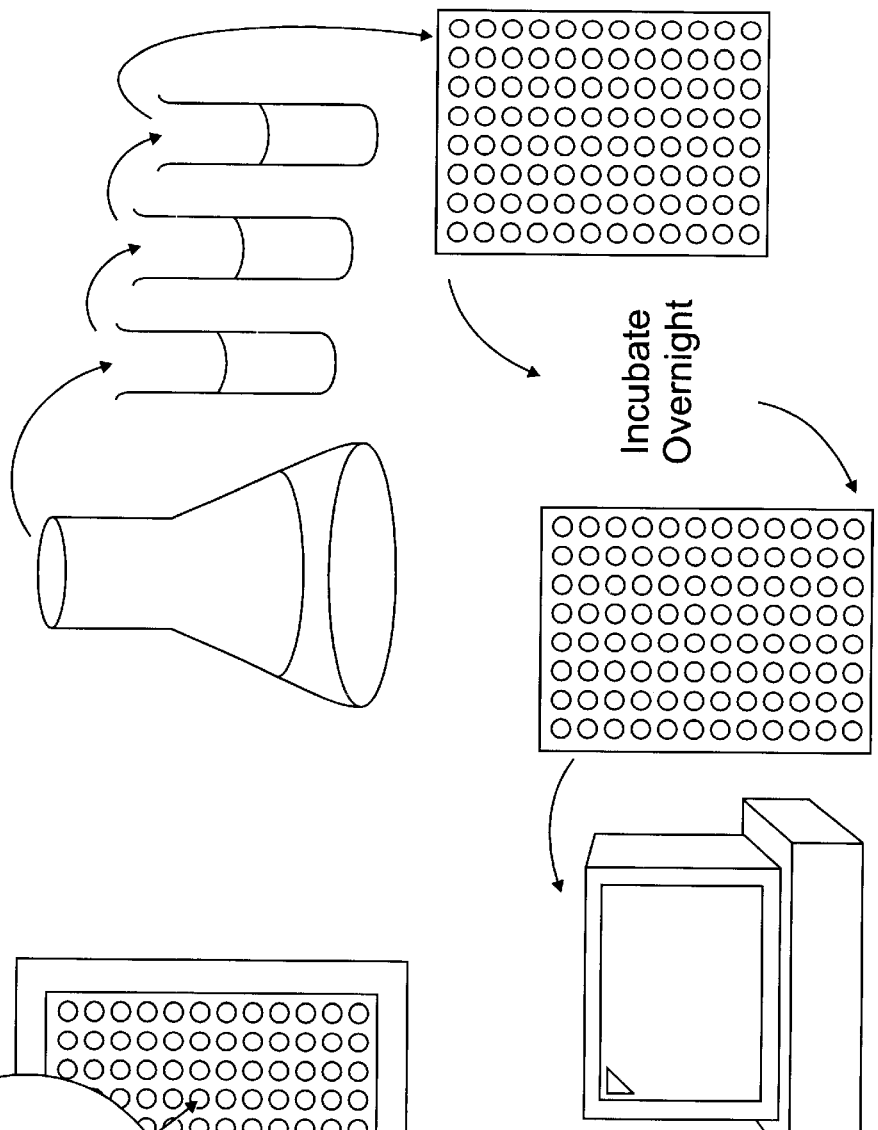
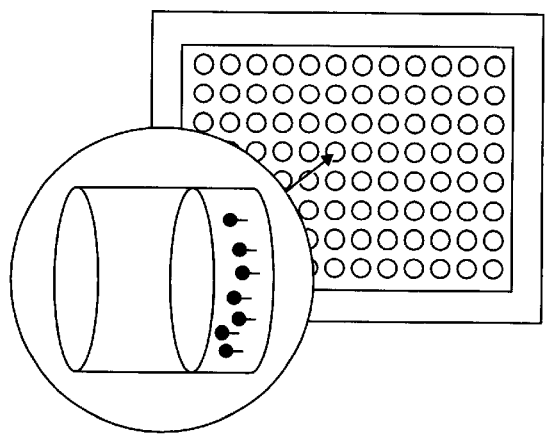
*Fig. 2B*
*Fig. 2A*
Incubate Overnight

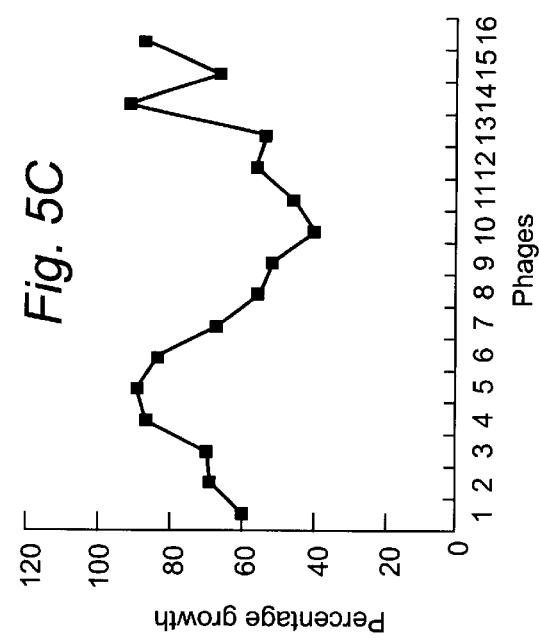
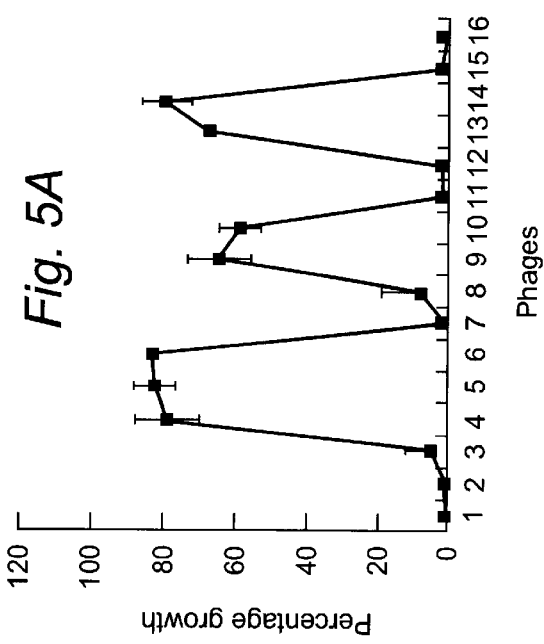
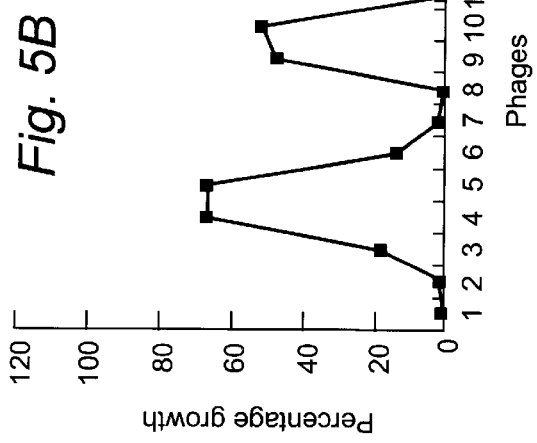
Fig. 5A
Fig. 5B
Fig. 5C

BACTERIOPHAGE ASSAY

This application is the U.S. national phase application of PCT International Application No. PCT/GB99/01363 filed Apr. 30, 1999.

BACKGROUND OF THE INVENTION

The present invention is concerned with the identification of bacteria, both by species and by sub-type, and to a new method of bacterial identification which relies upon bacteriophage specificity.

The control and epidemiology of bacterial outbreaks is becoming increasingly important and much effort is currently expended in identification of bacteria by species and sub-type. With the apparent continued rise in antibiotic resistant bacterial strains the need for careful and accurate identification of bacteria is becoming ever more critical.

Strain typing has been defined as "A pre-requisite to studying the epidemiology of bacterial pathogens and, ultimately, the development of control strategies" (see Smith et al, (1995) AEM 61:4263).

Typically identification of bacterial species and sub-types involves methods such as classifying bacteria according to their ability to grow using selected carbon sources, the specificity of bacteriophages for particular bacteria, or involves genetic analysis of the bacterial genome and comparison thereof to known genomic sequences (for example using techniques such as RFLP, RAPD, ERIC, PCR-RFLP or the like). For example strain differentiation in *Erwinia carotovora* subspecies *atroseptica* (hereinafter referred to as "Eca") is usually performed by serology, phage typing, carbon source utilization, genetic analysis or a combination of such techniques. All of the currently used methods are relatively time-consuming, causing delay in the positive identification of a sample. Minimisation of any delay may be vital for successfully controlling the spread of bacterial infections in the population generally or in selecting a suitable treatment regime for a patient.

For example, strain typing of bacteria may be carried out using bacteriophages (hereinafter referred to simply as "phages"). A phage is any virus whose host is a bacterium. Most bacteria can be infected by phages, which are a highly diverse group of viruses. A given phage can only infect one or a few strains or species of bacteria and this limitation of phage infectivity forms the basis of strain typing using phages. The outcome of phage infection depends upon the phage and its host cell, but can be classified into two main groups as follows:

Virulent phages: induce lysis of the host cell.
Temperate phages: can establish a stable non-lytic relationship with the host cell.

Conventionally, strain typing of an unknown strain of bacteria via phage infection involves plating out a single colony of bacteria obtained from a test sample onto an agar dish and, once a bacterial lawn is established, introducing inocula of a specific phage at discrete points. The inoculated plate is then incubated again before being examined by eye and the extent of degradation or lysis of the bacteria at the points where phage has been introduced is graded by the technician. The effect of various phages on the test bacteria are analysed.

The grading used to establish the extent of phage action on a bacterial colony will vary from complete lysis (and thus death) of the bacteria (due to successful replication of the phage) through to no effect noticeable to the eye (when the phage is unable to interact with the bacteria of the sample). Various grades between these two extremes also exist and to a large extent the accuracy of the test results depends upon the skill, experience and perception of the person reading the results and performing the grading procedure. Unfortunately, the subjective nature of the grading system means that ultimately the phage typing system lacks accuracy.

A typical analysis of *E. coli* O157:H7 by conventional phage typing methods is reported by Khakhira et al., in Epidermiol. Infect. (1990) 105:511–520, see especially Table 1 of this reference in this analysis there was visual assessment of 62 phage types and an attempt to assign a positive value to each result. The complexity of conventional bacterial strain typing by phage interaction is clear from the typical analysis results depicted in Table 1.

SUMMARY OF THE INVENTION

We have now found that the highly specific interaction between phages and bacteria can be used in a much more effective assay in which the results of the phage/bacteria interaction is determined through measurement of bacterial growth, rather than bacterial death. This novel approach to phage typing enables conventional techniques for observing bacterial populations, such as determining the optical density of a sample, to be successfully employed. Consequently the results do not rely on a subjective analysis but on a direct and reproducible reading of a characteristic of the test sample.

In the assay of the invention a predetermined amount of phage is combined with an isolate of bacteria, the mixture being located in a suitable container. The mixture of phage and bacteria is conveniently held in a liquid or semi-liquid medium facilitating interaction of the two species. Conveniently the phage is located in the container and the bacteria added to the phage. However the assay is not limited to this approach and also encompasses, for example, the bacteria being located in the container and the phage added thereto.

In one aspect the present invention provides an assay to identify bacteria present in a sample, said assay comprising the following steps:

(a) isolating a single colony of said bacteria;
(b) combining said isolated bacteria with a selected bacteriophage in a container, the combination of bacteria and phage being incubated in a medium containing the nutrients required for bacterial growth and which enables phage/bacteria interaction; and
(c) determining the extent of bacterial growth.

Where the phage interacts with the bacteria of the test sample, the phage will infect the bacteria and, depending upon the virulence of the phage, will either cause death of the bacteria or will slow bacterial reproduction. If the phage is unable to infect the bacteria, bacterial growth will be unaffected. Thus, determination of the extent of bacterial growth following incubation with the phage is a direct correlation of the interaction of the phage and bacteria. Since the phage will interact only with specific bacteria, the extent of bacterial growth in the assay provides information on the species or sub-type of the bacteria.

Thus the assay of the present invention will have utility as an in vitro method of diagnosis for bacterially based infections or diseases in plants, animals and humans. Additionally the assay has utility as a means of monitoring food or medicines etc. for bacterial contamination.

Suitable phages are commercially available from culture collections and conventional phage typing systems. In addition phages specific for particular bacteria can be engineered using routine techniques in the laboratory due to the phages' ability to rapidly mutate producing host range mutants. Alternatively suitable phages can be isolated from the natural habitat of the bacteria in question and again standard techniques and methodologies are well known and within the ability of the skilled technician.

One important feature of the present assay is to retain the phage of interest in a non-replicative state to avoid mutation of the phage prior to the assay. Similar requirements are imposed on the conventional method of phage typing and have not been found to be unduly onerous since if no bacteria are present, the phage will be unable to replicate or mutate.

Suitable media for incubation of the phage/bacteria combination include those conventionally used for growing bacterial cultures, for example nutrient broth (NB) or Luria Bertani (LB) broth. Conveniently the medium is liquid at the temperature of incubation since this assists the mixture of phage with the bacteria. It is essential that the medium chosen is compatible with the method used to determine the extent of bacterial growth. Thus if the optical density of a sample is used as a measure of bacterial growth, the medium chosen must enable the penetration of light through the sample. Liquid media are generally suitable for optical density measurements.

Conveniently, determination of the extent of bacterial growth may be obtained by measuring the optical density (OD) of the sample in accordance with conventional practice. The growth of the bacterial colony may be determined by obtaining the difference between an initial reading taken as soon as the bacteria and phage have been combined together-and a second reading taken after the period of incubation. Alternatively a control may be used to standardise a single reading of the sample taken following the period of incubation. Suitable control standards include the growth medium alone or the growth medium together with phage. A positive control consisting of bacteria and growth medium only may also be useful to obtain percentage growth readings. (Percentage growth is the median absorbance phage (n) well minus the base value (ie the ratio obtained when complete lysis occurs) divided by the median absorbance control well minus the base value). An alternative expression is infection ratios (see Table 1). (The Infection Ratio is the (mean) Absorbance control wells divided by the (mean) Absorbance phage (n) well.) To improve accuracy of the readings obtained it may be advantageous to run parallel tests in duplicate or triplicate and then average the results for each sample/phage combination.

Suitable optical density readings would normally be taken at wave lengths of 590–630 nm, usually at 595–600 nm. Equipment for reading the optical density of a sample is commercially available. Suitable apparatus includes microtitre plate readers.

In one preferred embodiment the phage is pre-located in the selected container and retained therein, for example by means of a fixant, by physical entrapment or by chemical interaction (eg ionic attraction) with the surface of the container. For example, we have successfully located the phage in microtitre plates using 5% gelatin as a fixant. Other polymers which may be suitable fixants include PVP, PVPP, alginate, albumins, starches, PVA, guar gum and the like. Conveniently the fixant used will physically retain the phage within the container during storage but on addition of the bacteria in a liquid growth medium the fixant will dissolve or otherwise release the phage for interaction with the bacteria. Other means of retaining the phage includes electrostatic attraction of the charged phage particle with oppositely charged groups on the surface of the container or retention of the phage on a porous surface, for example on a porous membrane. Alternatively, the phage may be freeze dried onto the container and the freeze dried phage may then optionally be coated. Again freedom of the phage to interact with the bacteria is important.

Such techniques of retaining the phage within the selected container has the advantage of enabling the container to be stored for relatively long periods of time without any concern that cross-contamination of particular phage into an adjacent container may occur or that the phages will lose their viability. As a result it is possible to prepare multiple containers, for example microtitre plates, in which the containers have been pre-loaded with phages of different specificities. In this way a profile of the bacterial colony under test may be obtained. Microtitre plates have the additional advantage of co-operating with standard laboratory equipment such as microtitre OD readers.

In the assay of the present invention the ratio of bacteria:phage is important and it may be necessary to perform routine test dilution of the bacterial colony to obtain a suitable ratio. This ratio is necessary to a) allow bacteria to grow and become infected, while preventing external cell lysis by phage enzymes, b) to prevent overgrowth of the bacteria in the presence of too few phages.

Table 1 shows an exemplary micro-titre plate layout of phages and bacterial strains indicating optical density values. Column 0 contains no phage. Columns 1–11 contain different phages. Row A contains the positive control strain, sensitive to all the phages; row B contains growth medium only, rows C to E contain 3 replicates of strain 1; rows F to H contain 3 replicates of strain 13. Well A0 (control strain in the-absence of phage) is used to obtain infection ratios.

According to a further aspect the present invention provides a container having a specific phage subtype located therein, said phage being retained in said container by a fixant, physical entrapment or chemical interaction with the surface of the container. In a preferred embodiment the present invention provides a microtitre plate, wherein wells of said plate are said containers. Preferably different specific phage subtypes are located in different wells on the same plate.

Such pre-prepared plates may be designed to identify particular sub-types of bacteria (eg *E. coli* O157) from other related sub-types of the same species. Alternatively the plates may be designed to identify bacterial species. The plates may be stored until required.

The present invention may have utility in the following situations:

a) typing bacterial plant pathogens for epidemiological analysis. Examples include Pseudomonas spp, Xanthomonas spp, Erwinia spp, (including *Erwinia carotovora* subspecies *atroseptical*) and the like.

b) typing human and animal bacterial pathogens for epidemiological analysis. Examples include Salmonella, Campylobacter, Staphylococcus, Streptococcus, Escherichia, Pseudomonas, Listeria, Shigella, Vibrio, Serratia, Bacillus, Klebsiella, Mycobacterium and the like.

c) typing bacteria which cause water and/or food contamination or which are present in hospitals and/or food processing areas, or monitoring for such bacteria. A specific example concerns Lactococcus spp. which play an important role in the milk fermentation process during the production of cheese and cultured dairy products. These processes are susceptible to phage contamination and so typing can be used to monitor the phage susceptibility of the cultures used.

d) rapid screening of *Mycobacterium tuberculosis* isolates using microtitre plates containing specific phages for phage therapy.

e) typing biological pesticides such as *Bacillus thuringiensis*.

Phages may be located in a container along with other tests in different wells so that on a single, eg microtitre, plate toxin types, plasmid types, specific identifying sequences of DNA/RNA, chemical susceptibility and resistance, and antibody specificities may be tested.

A suitable protocol for the use of such plates is set out below.

Protocol (assuming isolated bacterial colonies) (see FIGS. 1A–1E, 2A–2B and 3);

1) Grow bacterial isolates overnight in a suitable growth medium.
2) Dilute the cells to pre-determined cell density in same medium (for example Luria Bertani broth).
3) Add the cells (150 μl per well) to a pre-prepared microtitre plate containing phages in wells thereof using a multi-channel pipette or other means.
4) Incubate the plate overnight.
5) Read the plate in a micro-titre plate reader or stack the plate on an automatic feeder.
6) Once the plate has been read, identify the bacterial isolates of interest from the output information (conveniently a printout or computer display) which indicates bacterial growth in each well and compares the interaction of the sample with the phage sub-types used relative to known standards (for example, pre-selected profiles).

Thus, in one embodiment of the invention phages specific to the bacterium of interest are added to wells in a micro-titre plate, fixed in a matrix which allows the phages to survive but prevents them from cross-contaminating other wells in the plate. Suitable fixation has been achieved using 5% gelatin, although other matrices or methods of fixing the phages could be employed, eg polyvinylpyrrolidone (PVP) or freeze drying. Once the phages have been fixed into the wells the plates can be stored until needed. The storage time depends on the viability of the phages but would typically be at least 6 months and may be several years.

To type a bacterial isolate it is grown overnight in a suitable growth medium and diluted in that medium to a pre-determined concentration. The optical density is taken before dilution to estimate the number of cells present and the dilution factor needed, since after dilution too few cells are present to obtain an accurate reading. A suitable concentration would be in the region of $10^3$–$10^5$ cells/ml to prevent overgrowth of the bacteria in the wells. An appropriate volume of the diluted cells (typically 150 μl ) is then added to each individual well using a multi-channel pipette.

Each well (other than the non-phage containing controls) will also contain one phage type of a total of up to approximately 45 different phage types (conveniently one phage type of a total of 19 or 11 different phage types, depending upon the need for replication of each assay (see FIG. 4)) with each phage type being located in a separate well. Controls include (1) cells in the absence of phage (to ensure cells are able to grow in the absence of phage), and (2) phage plus growth medium in the absence of cells (to monitor plate contamination). All samples and controls may be performed in triplicate to increase reproducibility. After over-night incubation at a temperature suitable for phage adsorption and replication, the micro-titre plate is read on a plate reader at 595 nm and an OD reading obtained for each well (see Table 1). The temperature used for incubation will depend upon the bacteria under study. For example an incubation temperature of approximately 25° C. would be suitable for Erwinia and an incubation temperature of approximately 37° C. would be suitable for *E. coli*. In the absence of phage action, cells grow and produce OD values of approximately 0.5 (although the extent of cell growth and thus the OD reading may vary between bacterial strains). In the presence of phage action, cells are either killed or their growth is reduced, thereby lowering OD values. In the event of total cell death OD values can be as low as those of the control (2) where no bacteria were added.

A computer program can be set up for analysis of the incoming data and it is envisaged that a database of the results for various phage/bacteria readings could be established. The median of OD values may be taken (assuming at least three replicates) and the "percentage growth" calculated by comparing the median OD value with the OD of bacterial growth in the absence of phage (positive control) (Table 2).

$$\text{Percentage growth} = \frac{T - C_1}{C_2 - C_1}$$

Where:
T=median of phage/bacteria OD readings.
$C_1$=lowest OD value obtained after complete cell lysis.
$C_2$=median of OD readings for bacteria in the absence of phage.

Percentage growth values will be used to produce a "growth profile" for a particular strain (FIGS. 5–10). The assay of the invention therefore offers much greater discriminatory power than traditional phage typing which in most cases gives a positive or negative result only.

If a particular strain(s) is being sought/tracked, this strains infection profile could be pre-selected and the program asked to identify all plates/rows containing similar profiles.

For example, this would be very useful for epidemiological analysis of a particularly pathogenic strain during a hospital infection. In addition, a database containing all previously tested isolates, together with location and date of isolation etc., could be searched and patterns of dissemination identified. Although some variation in percentage growth occurs (FIGS. 5A–5C, 6, 7A–7B and 10A–10B), such variation could be taken into account by the computer program when assessing profile similarities.

Extensive testing of the system has already been undertaken for use with the plant pathogen *Erwinia carotovora* subspecies *atroseptica* (Eca) and the human pathogen *E. coli* O157:H7, and has been found to be simple, rapid and reproducible (FIGS. 5A–5C, 6, 7A–7B and 10A–10B). Eca is widespread in temperate regions and its control is of commercial importance to the potato seed industry as Eca is responsible for soft rot of potato tubers in the field and in storage, as well as blackleg of potato plants.

*E. coli* O157:H7 causes potentially fatal food poisoning and is a problem worldwide. Much attention is currently being given to the epidemiology of this pathogen on farms, in the food industry and in hospitals.

Recently there has been some interest in the use of phages as a means of controlling infections of antibiotic resistant strains of bacteria. The assay of the present invention can be used as a means of identifying a phage which is efficient at causing cell death in any particular bacterial species or sub-type.

In a further aspect the present invention also provides an assay to identify a bacteriophage able to combat replication of a specific bacterial species, said assay comprising:

(a) isolating a single colony of said bacteria;
(b) combining said isolated bacteria with a selected bacteriophage, said combination being held in a liquid medium containing the nutrients required for bacterial growth and incubating said combination;
(c) determining the extent of bacterial growth; and
(d) selecting any bacteriophage which has significantly depressed the extent of bacterial growth.

Optionally, the assay may be combined with other tests on the same plate for rapid analysis of bacterial isolates.

The present invention also provides a method of treating a bacterial infection in a plant, animal or human, said method comprising selecting a bacteriophage specific to the bacterial strain causing the infection by means of the assay as decribed above and administering a suitable dose of the bacteriophage so selected.

The present invention will now be further described with reference to the following (non-limiting) Example and Figures in which:

BRIEF DESCRIPTION OF THE DRAWINGS

FIGS. 2A–2B Schematic representation of novel phage typing system. Phages are fixed in microtitre-plate wells to allow storage and convenience of use. Bacterial colonies are diluted to a predetermined density and a fixed volume added to each well. After over-night incubation, appropriate to the bacteria being typed, plates are read in a microtitre plate reader followed by data storage in a database for later retrieval.

FIGS. 5A–5C Analysis of five *E. coli* O157:H7 strains, FIG. 5A) 1291, 3895 and 3939, FIG. 5B) 3602, and FIG. 5C) 3946, all of which belong to phage type 28 when analysed by conventional phage typing but show three types when analysed by new method. In FIG. 5A, bars show standard deviations of greater than 5%.

FIG. 7A) Analysis of *E. coli* O157:H7 strain 3964 (phage type 2 by conventional phage typing) repeated five times with three replicates in each case. FIG. 7B) Analysis of seven strains, five belonging to phage type 2 (322, 1563, 3487, 3932 and 3964) and two classified as RDNC by conventional phage typing. Bars show standard deviations of greater than 5%.

DETAILED DESCRIPTION OF THE INVENTION

Example

Methods

Figure 1A:
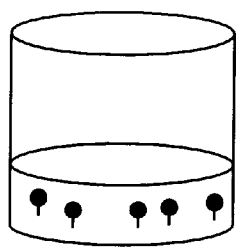
FIGS. 1A–1E Procedure for novel phage typing system.
Figure 1B:
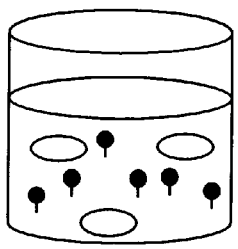
Figure 1C:
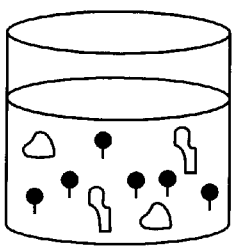
Figure 1D:
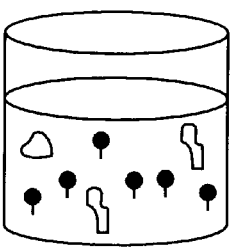
Figure 1E:
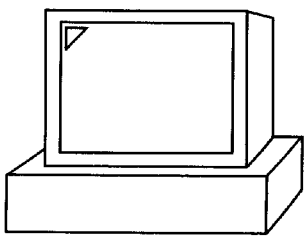
Figure 3:
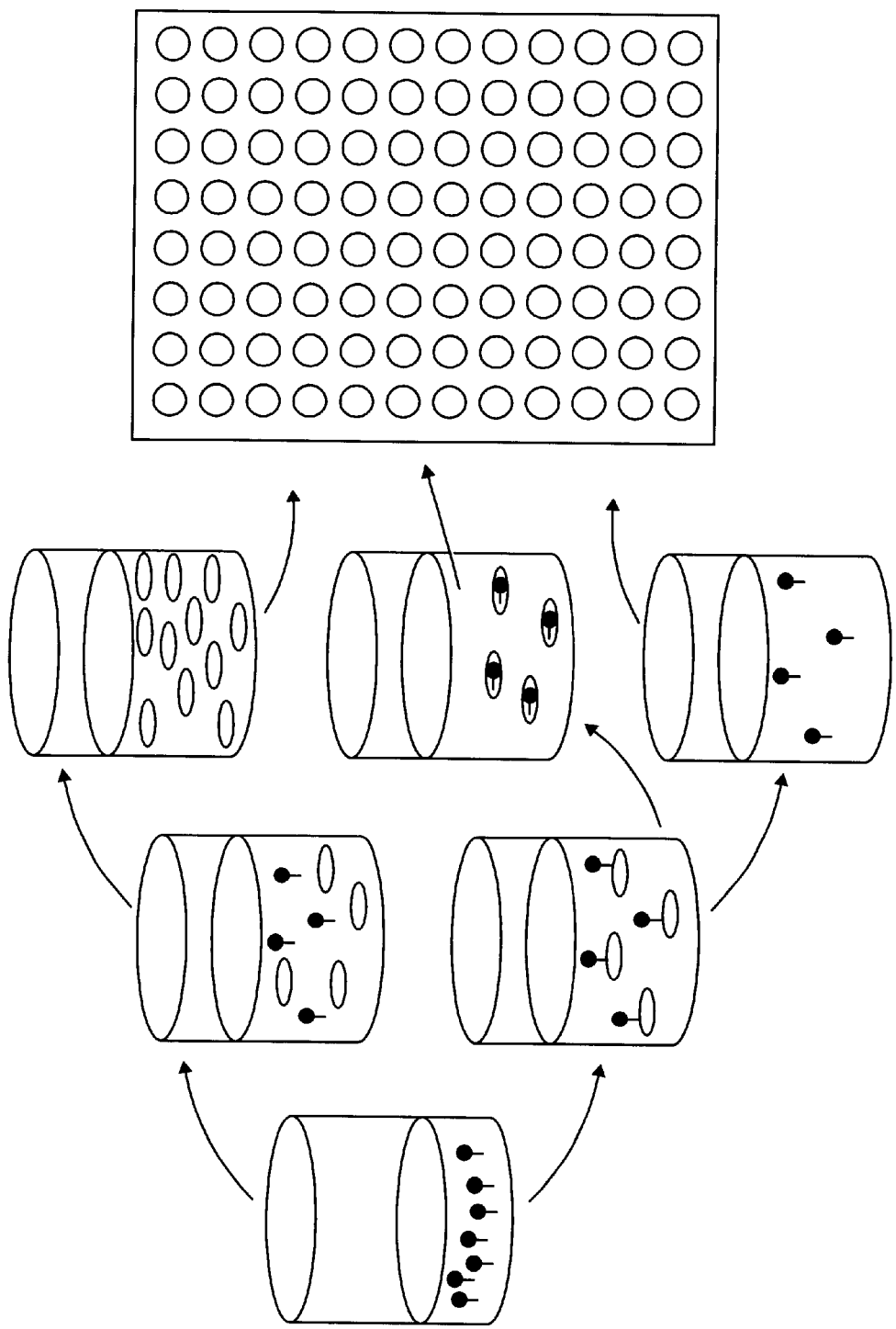
FIG. 3 Schematic representation of novel phage typing system. If phages fail to infect bacterial cells, these cells grow in media increasing its optical density. If phages infect cells, lysogeny of lysis may occur reducing or preventing cell growth and altering optical density accordingly.
Figure 4:
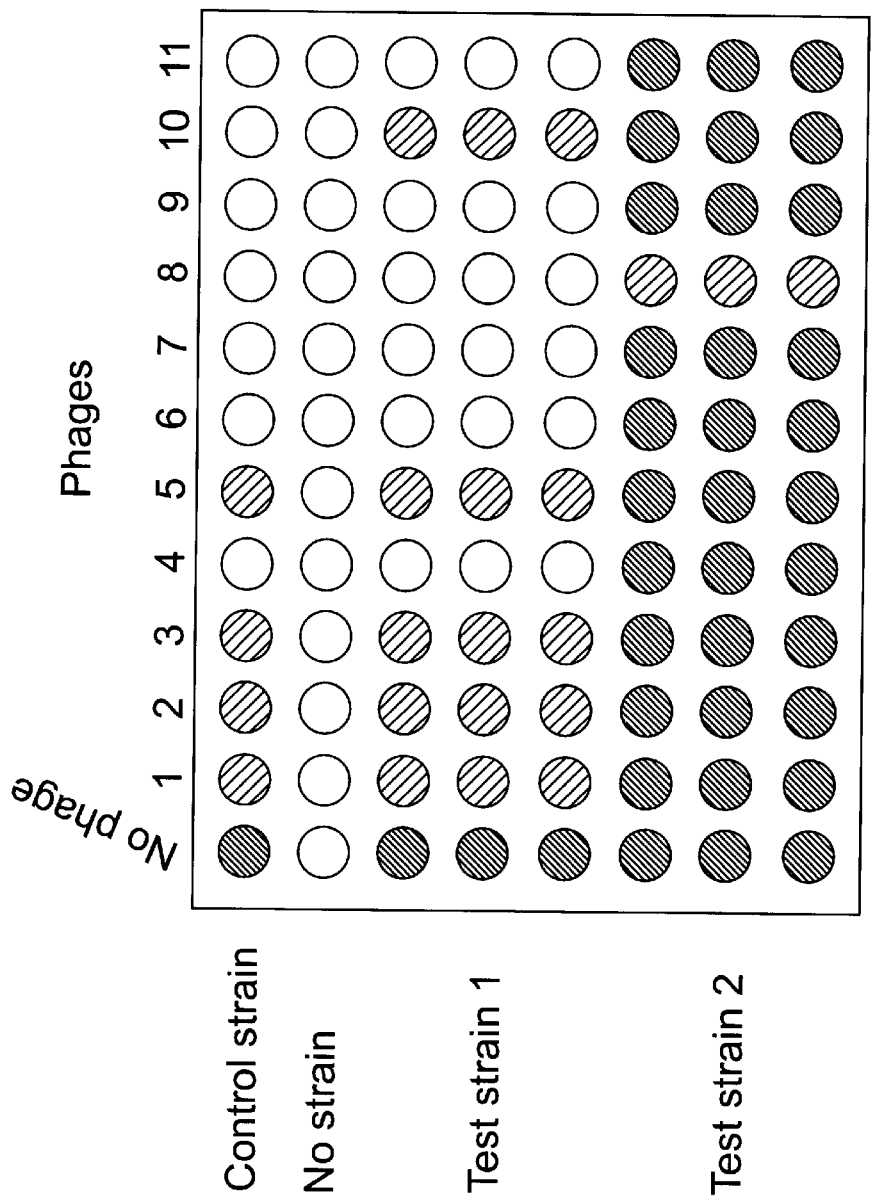
FIG. 4 Micro-titre plate layout of phages and bacterial stains. Column 0 contains no phage. Columns 1–11 contain different phages. Row 1 contains the positive control strain, sensitive to all the phages; row 2 contains growth medium only, rows 3 to 6 contain 3 replicates of strain 1; rows 7 to 10 contain 3 replicates of strain 2. Well A0 (control strain in the absence of phage) is used to obtain infection ratios.

Computer-assisted phage typing: Phages at routine test dilution, determined for both sets of phages, were added to 5% sterile gelatin, previously, and 5 µl added to selected wells in a 96 well sterile microtitre plate. In the case of Eca phages only, microtitre plates were stored at 4° C. for up to one month until required. Based on optical density values at 595 nm and 630 nm respectively, Eca and *E. coli* O157 cells were diluted to ca. $10^3$ cells $ml^{-1}$ and 150 μl added to microtitre plate wells before overnight incubation at 25° C. and 37° C. respectively. The following day the optical density of each well was read on a spectrophotometry (Dynatec) at 595 nm or 630 nm, for Eca and *E. coli* respectively. Each strain was tested in triplicate. Since 11 phages and 16 phages were used for Eca and *E. coli* respectively, plate layouts were designed differently (FIG. 4).

Analysis of data: The median of three optical density values for each strain was taken and the median value in the presence of a particular phage minus the base value (the value obtained in the case of complete cell death in the presence of a phage) was divided by the median value of the control wells containing no phages minus the base value. This value was then multiplied by 100 and termed "percentage growth".

i.e. percentage growth =

$$\frac{\text{median optical density phage [n] well} - \text{base value}}{\text{median optical density control well} - \text{base value}} \times 100$$

Results

Figure 6:
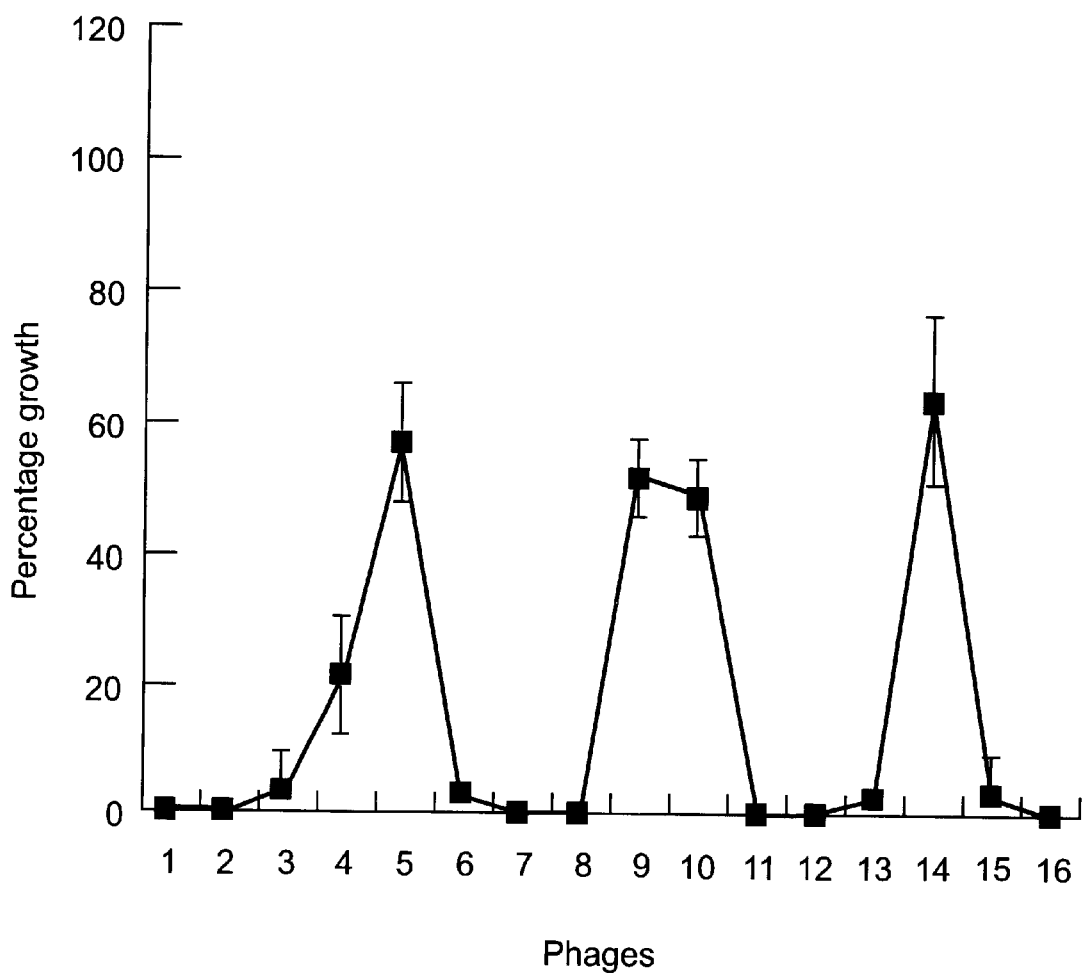
FIG. 6 Analysis of *E. coli* O157:H7 strain 3694 (phage type 54 by conventional phage typing) together with six RDNC strains, 643, 644, 645, 646, 647 and 648 all of which appear to fall into the same phage type as 3694. Bars show standard deviations greater than 5%.
Figure 7A:
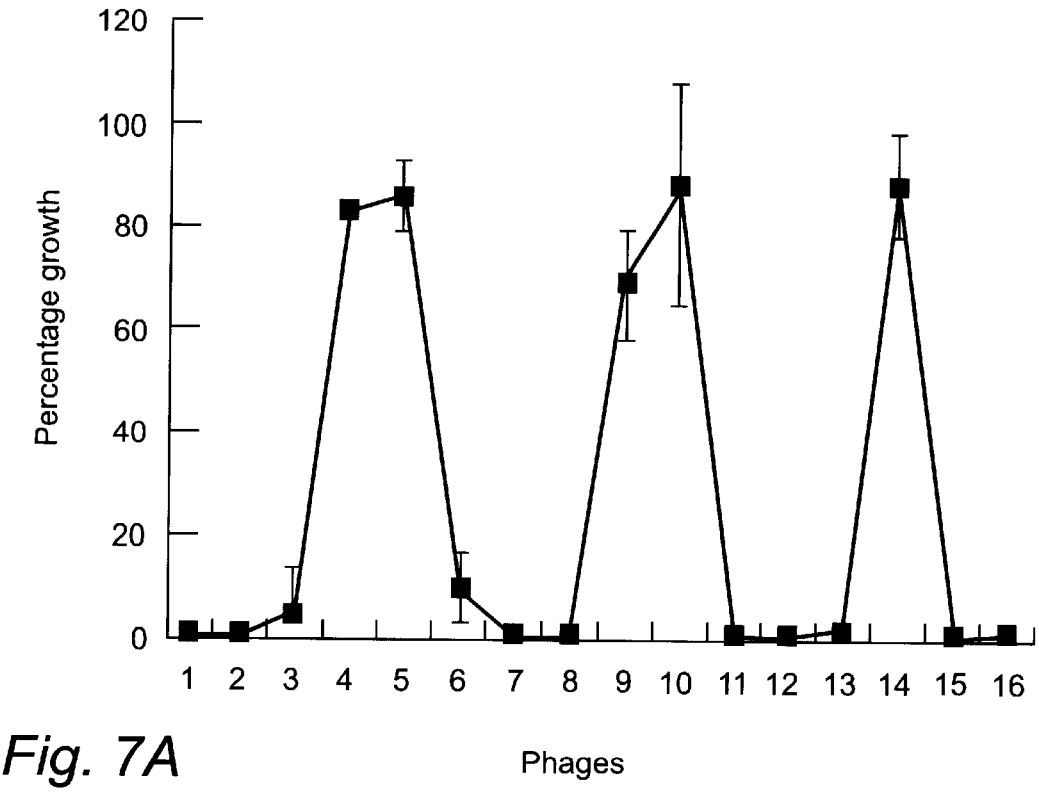
FIGS. 7A–7B.
Figure 7B:
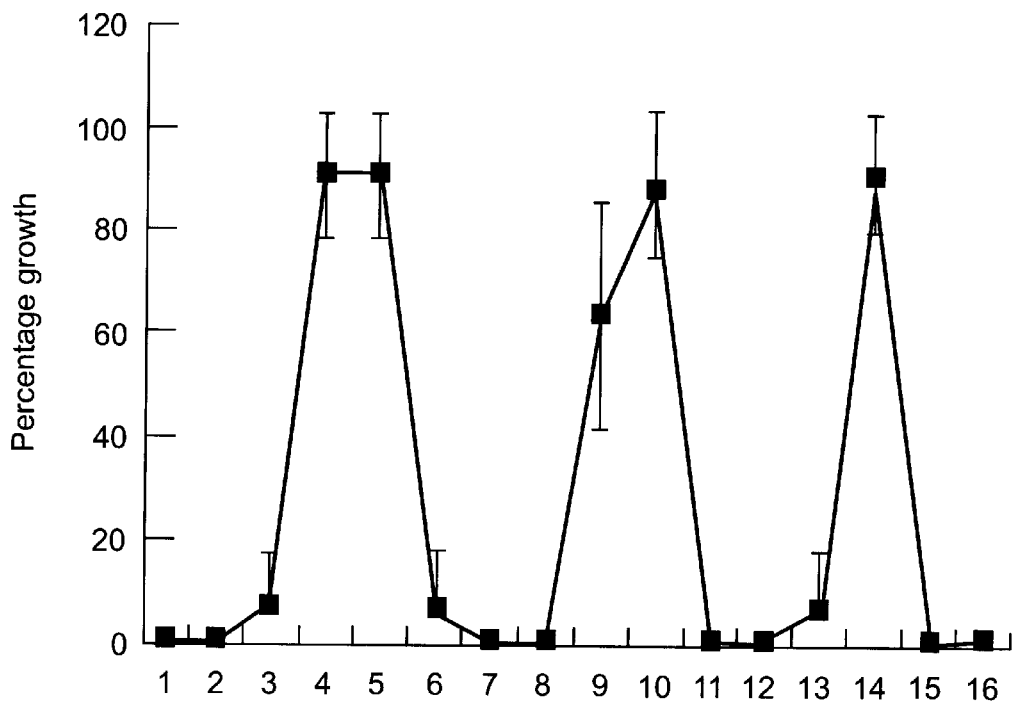
Figure 8A:
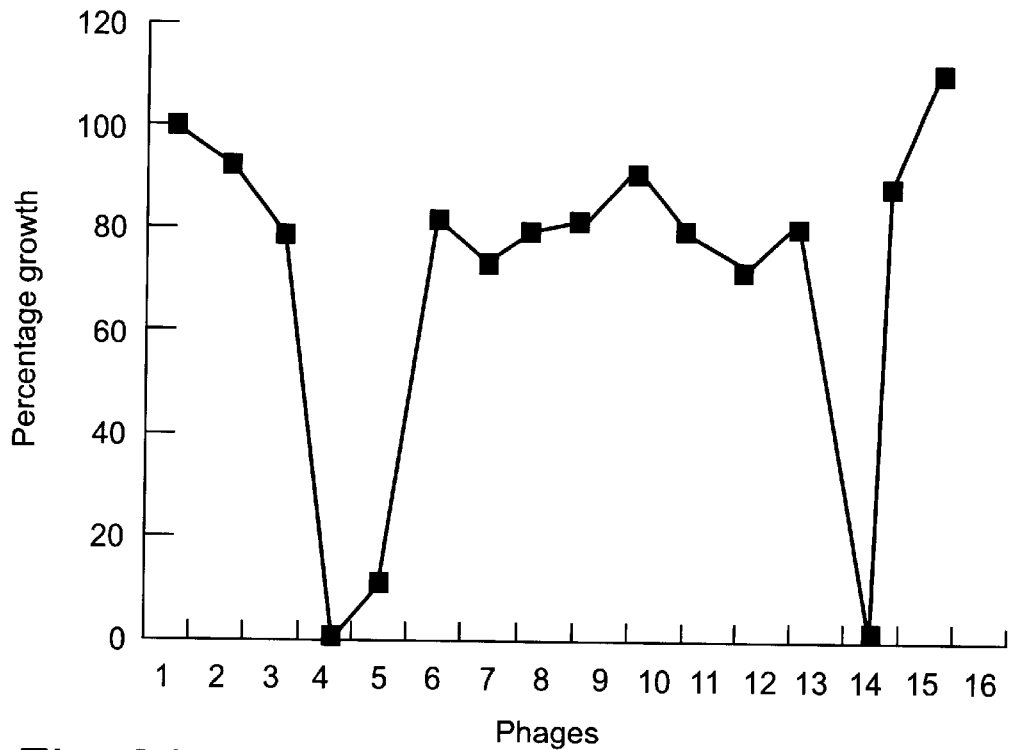
FIGS. 8A–8F Growth profiles of *E. coli* O157:H7 strains from FIG. 8A) RDNC strain 921, FIG. 8B) RDNC strain 936, FIG. 8C) RDNC strain 3690, FIG. 8D) strain 3890 (phage type 4 by conventional phage typing), FIG. 8E) Non-O157 *E. coli* strain control 530 0111. Using conventional phage typing strains FIGS. 8A–8D do not fit into any of the conventional phage types and are classified accordingly as RDNC (react but do not conform). Each strain was analysed in triplicate on a single microtitre plate.
Figure 8B:
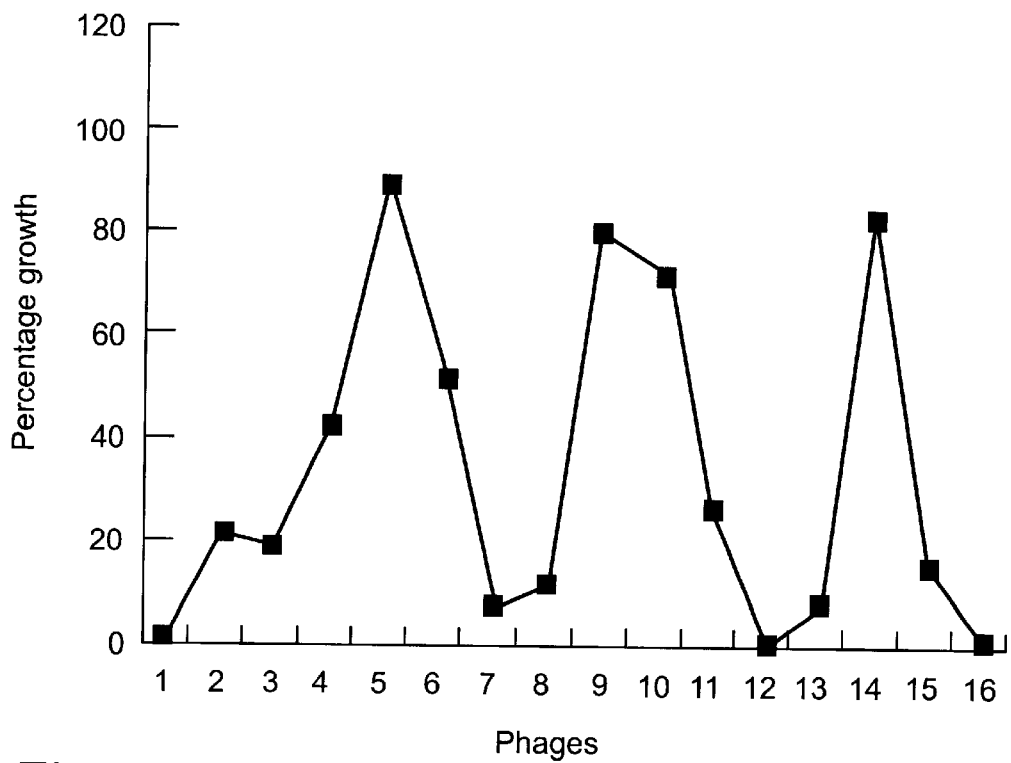
Figure 8C:
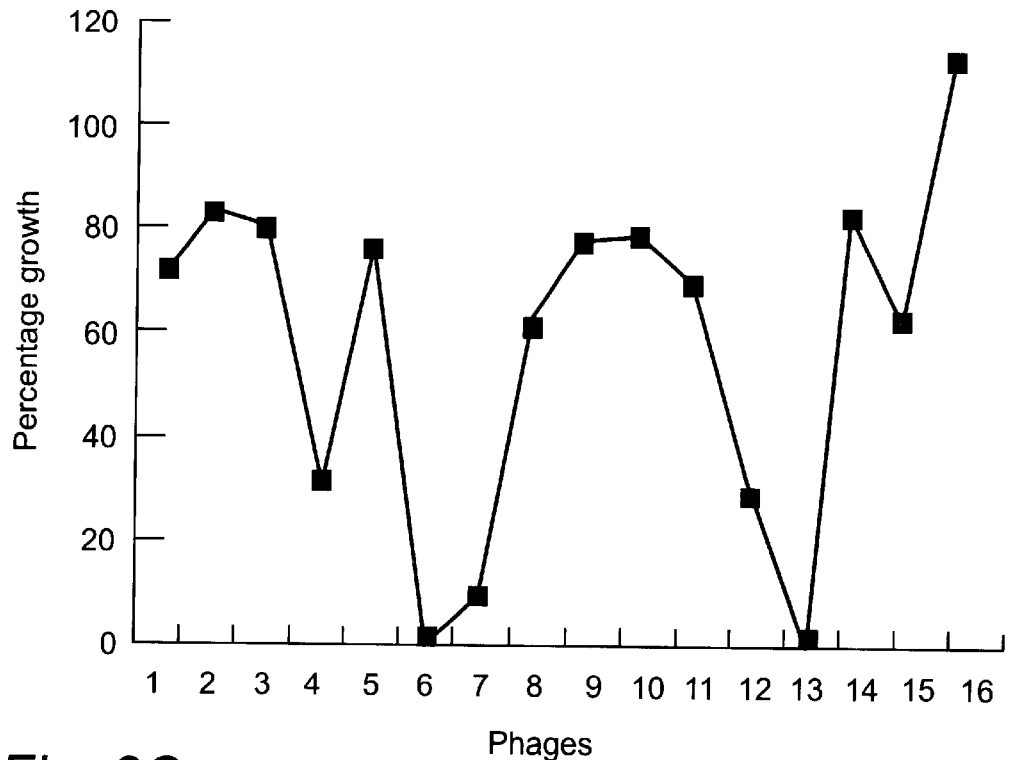
Figure 8D:
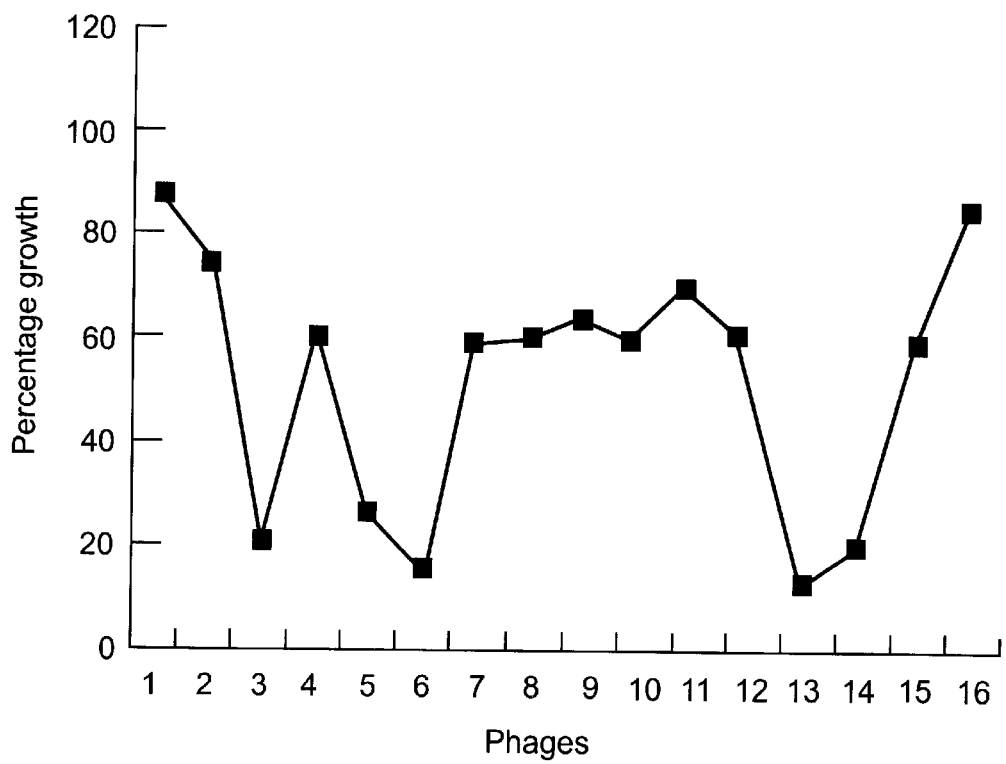
Figure 8E:
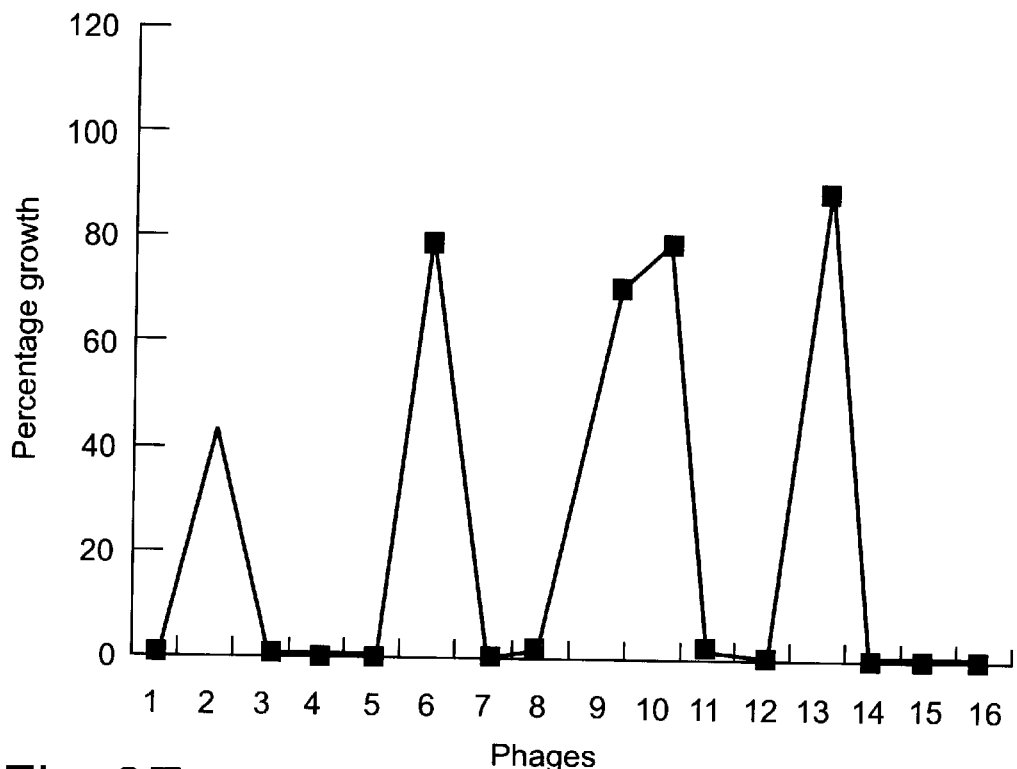
Figure 8F:
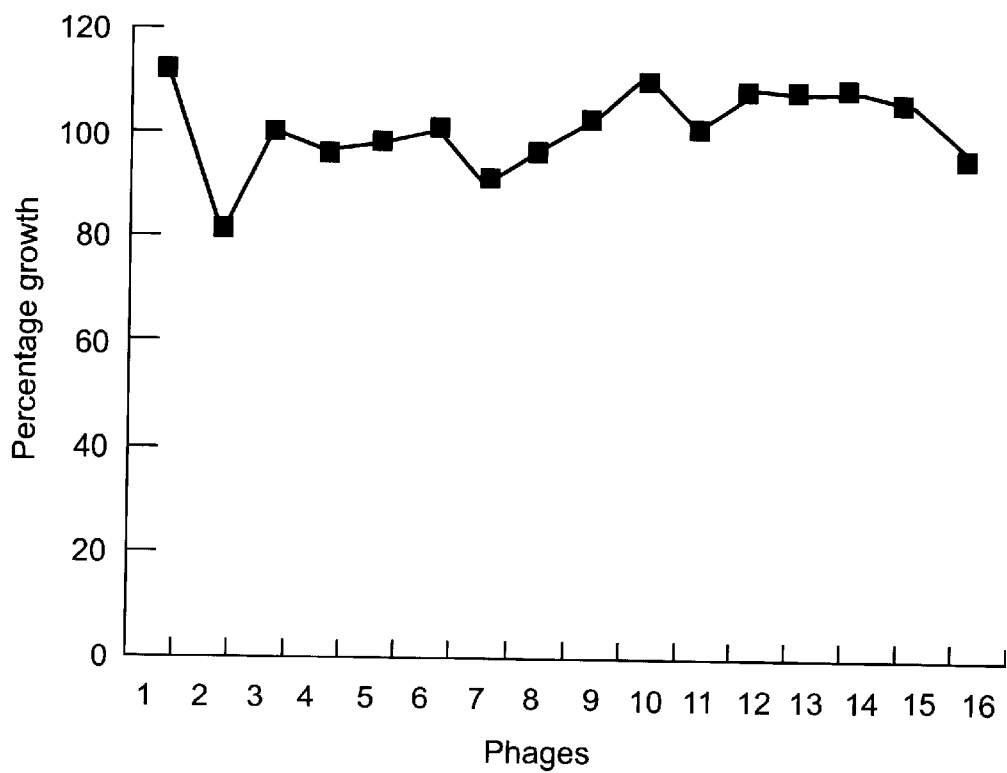

*E. coli*: The percentage growth was obtained for each *E. coli* O157 isolate and results compared to conventional phage typing (Table 3). In general, isolates belonging to a particular phage type gave related patterns using the novel method. However, the advantage of the novel system over conventional phage typing was seen when: a) isolates with a conventional phage type showed different growth patterns using the novel method, e.g. 3946, 3602 (phage type 28) showed different patterns to other isolates within this phage type, indicating that either these isolates had been misclassified by the conventional method or that the novel method was able to differentiate between isolates within this phage type (FIGS. 5A–5C). Similar findings were seen within phages type 2 and 49; b) all RDNC (React but Does Not Conform) isolates were typeable using the novel system. These isolates, so called because of their failure to give consistent phage typing patterns and therefore their failure to fall into a conventional phage type, were differentiable using the novel method. Five RDNC isolates, 644, 645, 646, 647 and 648, isolated from a single source/outbreak, gave growth patterns consistent with phage type 54 (FIG. 6). Similarly RDNC isolates 714 and 785, again isolated from a single source/outbreak, gave growth patterns consistent with phage type 2 (FIGS. 7A–7B). Four other RDNC isolates gave unique growth patterns using the novel system which did not match any of the phage types tested (FIGS. 8A–8F). However, of these four isolates, one had a unique pattern compared to other RDNC isolates when typed by conventional phage typing, and another RDNC isolate was the only isolate tested to possess verotoxin 1 but not verotoxin 2 (Table 3). The novel method was found to be highly reproducible when percentage growth values were compared between isolates falling into a given phage type (FIGS. 5A–5C, 6, 7A–7B).

Figure 9A:
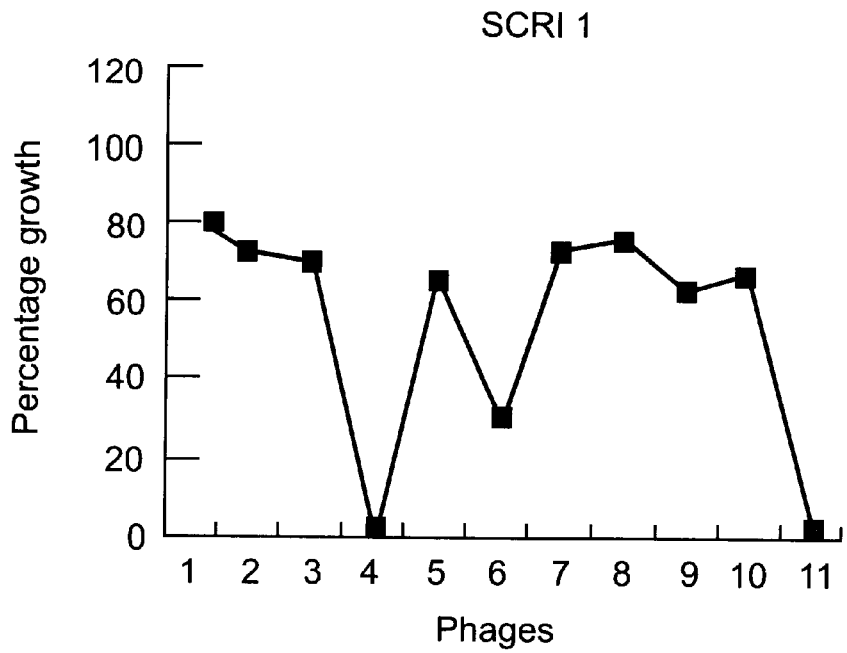
FIGS. 9A–9C Analysis of *Erwinia carotovora* subsp. *atroseptical* strains FIG. 9A) SCRI 1 and SCRI 98, FIG. 9B) SCRI 1050 and SCRI 48, FIG. 9C) SCRI 13 and SCRI 87. In each pair FIG. 9A, FIG. 9B and FIG. 9C, both strains give identical phage types by conventional phage typing. Each strain was analysed in triplicate.
Figure 9A:
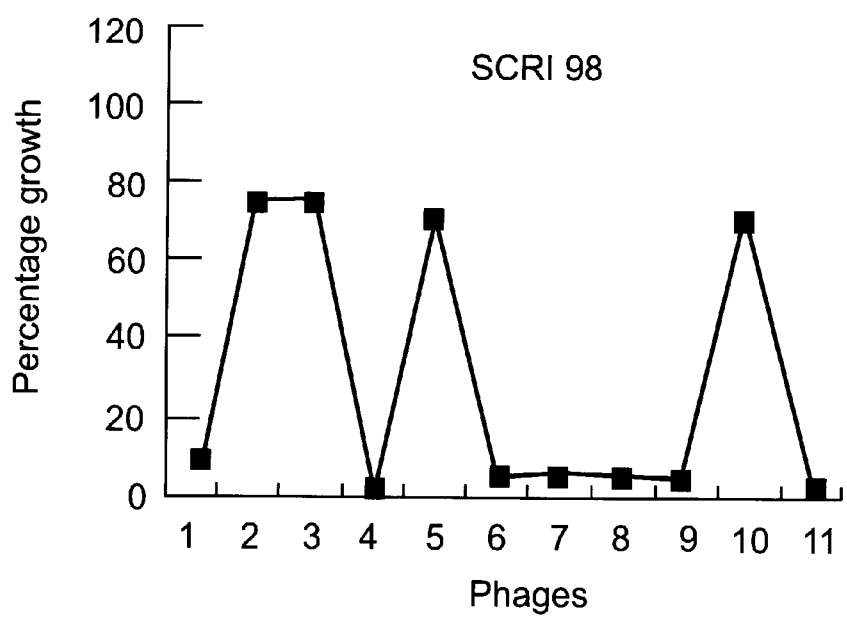
Figure 9B:
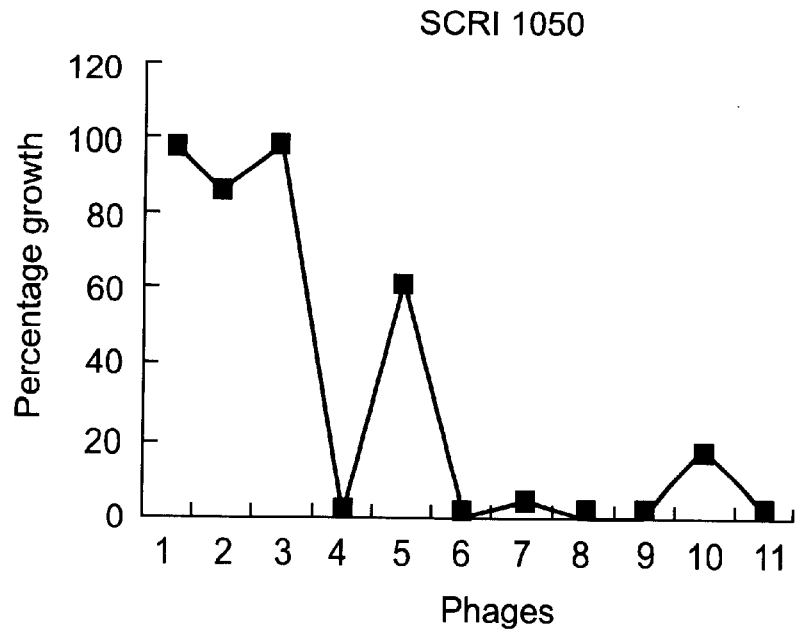
Figure 9B:
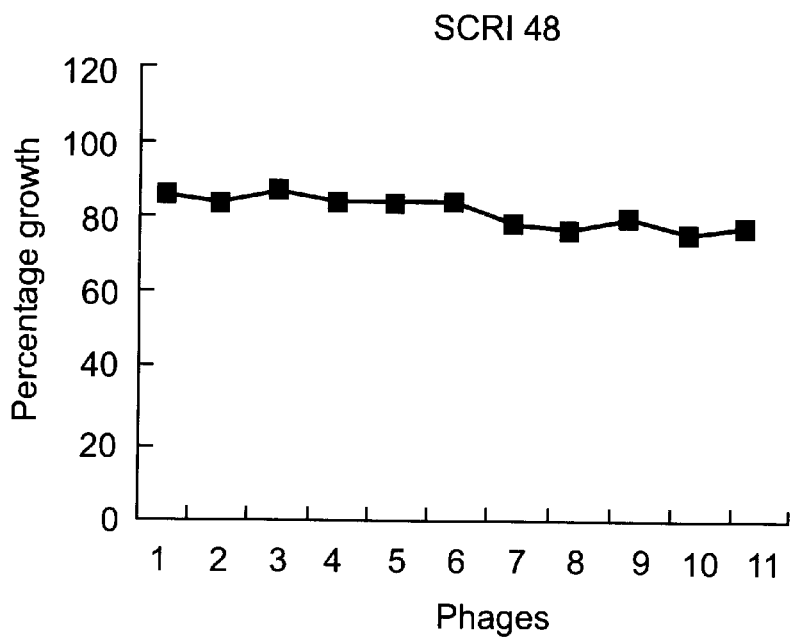
Figure 9C:
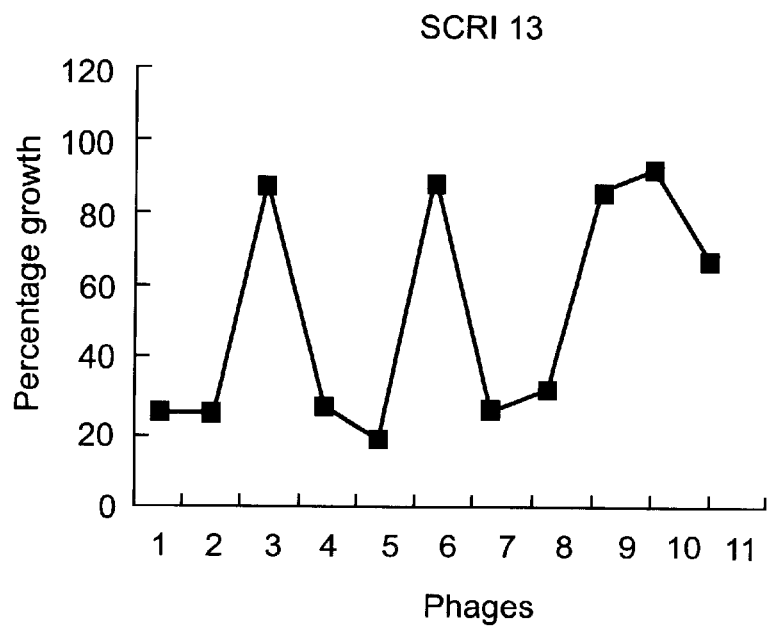
Figure 9C:
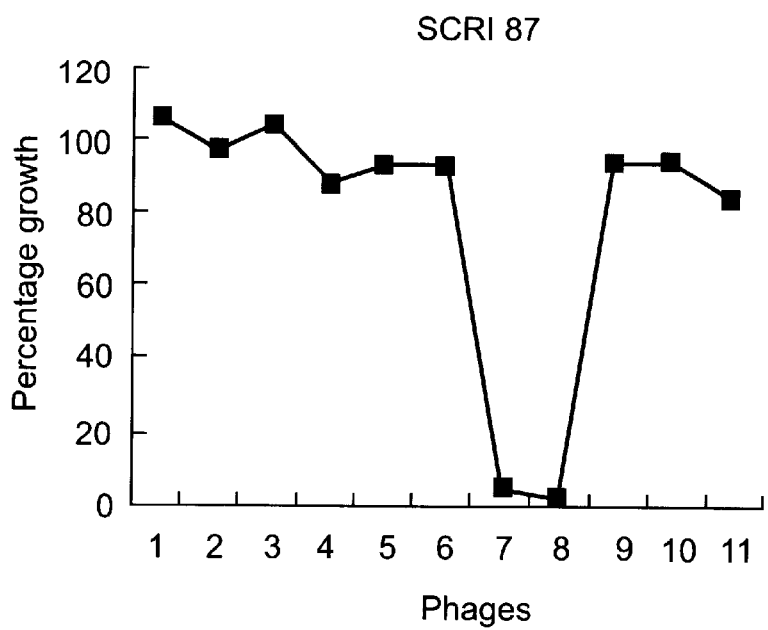
Figure 10A:
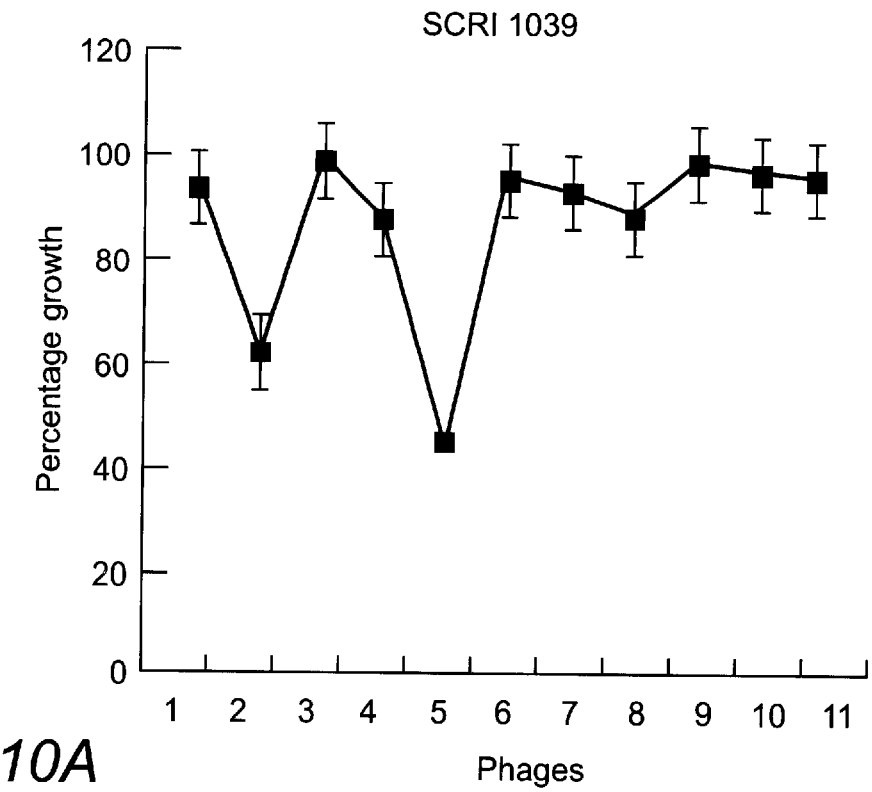
FIGS. 10A–10B Analysis of *Erwinia carotovora* subsp. *atroseptical* strains FIG. 10A) SCRI 1039 representing 14 replicates from 12 different microtitre plates and FIG. 10B) SCRI 1043 representing 16 replicates all from different microtitre plates. Bars represent standard deviations of greater than 5%.
Figure 10B:
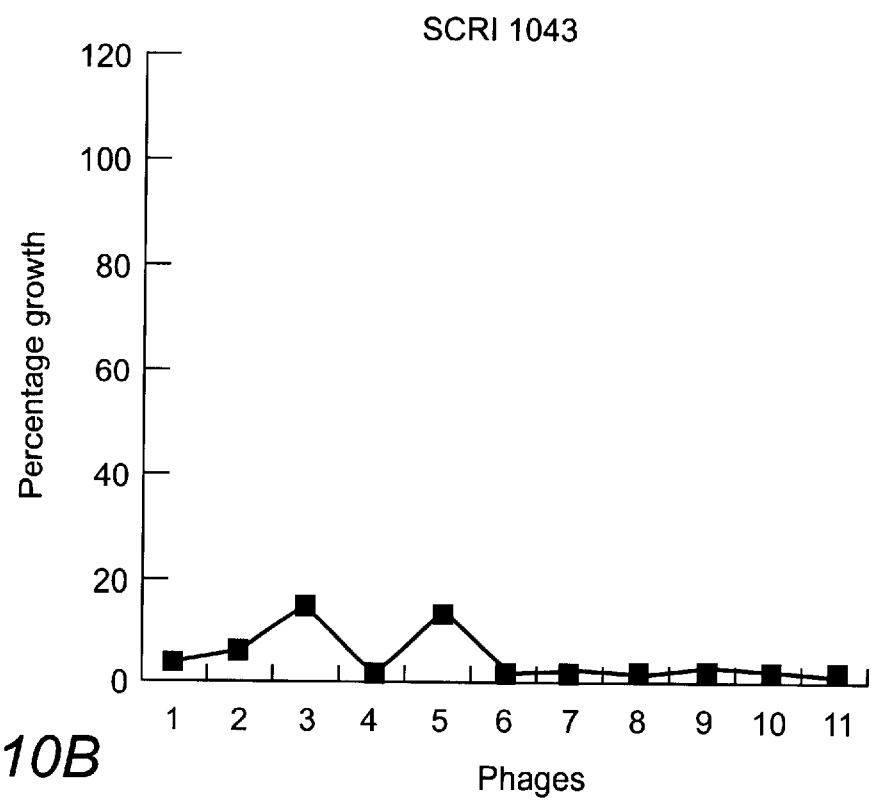

Eca: Phage typing using the novel method produced a large variation in phage types for Eca. Interestingly, a number of isolates which gave identical phage typing patterns using the conventional method, were clearly distinguishable using the novel method (FIGS. 9A–9C), thus adding to the discriminating power of the method. As in the case of *E. coli*, the novel method proved to be highly reproducibility. For example, percentage growth values, when tested on 14 and 16 replicates of Eca SCRI 1039 and SCRI 1043 respectively, showed little variation in standard deviation between replicates. In the case of SCRI 1043, this deviation was below 5% for all phages (FIGS. 10A–10B).

TABLE 1

| | Bacteriophages | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| A | T1 | T2 | T3 | T4 | T5 | T6 | T7 | T8 | T9 | T10 | T11 | T12 |
| | 0.448 | 0.108 | 0.094 | 0.135 | 0.053 | 0.124 | 0.054 | 0.055 | 0.053 | 0.054 | 0.074 | 0.055 |
| B | T13 | T14 | T15 | T16 | T17 | T18 | T19 | T20 | T21 | T22 | T23 | T24 |
| | 0.054 | 0.052 | 0.054 | 0.053 | 0.053 | 0.053 | 0.053 | 0.053 | 0.053 | 0.053 | 0.054 | 0.054 |
| C | T25 | T26 | T27 | T28 | T29 | T30 | T31 | T32 | T33 | T34 | T35 | T36 |
| | 0.181 | 0.139 | 0.132 | 0.139 | 0.051 | 0.134 | 0.079 | 0.145 | 0.146 | 0.130 | 0.135 | 0.051 |
| D | T37 | T38 | T39 | T40 | T41 | T42 | T43 | T44 | T45 | T46 | T47 | T48 |
| | 0.155 | 0.162 | 0.177 | 0.139 | 0.051 | 0.130 | 0.089 | 0.142 | 0.151 | 0.117 | 0.134 | 0.052 |
| E | T49 | T50 | T51 | T52 | T53 | T54 | T55 | T56 | T57 | T58 | T59 | T60 |
| | 0.184 | 0.153 | 0.141 | 0.146 | 0.052 | 0.136 | 0.103 | 0.117 | 0.145 | 0.152 | 0.138 | 0.052 |
| F | T61 | T62 | T63 | T64 | T65 | T66 | T67 | T68 | T69 | T70 | T71 | T72 |
| | 0.425 | 0.163 | 0.164 | 0.381 | 0.167 | 0.132 | 0.388 | 0.155 | 0.212 | 0.382 | 0.396 | 0.302 |
| G | T73 | T74 | T75 | T76 | T77 | T78 | T79 | T80 | T81 | T82 | T83 | T84 |
| | 0.417 | 0.160 | 0.168 | 0.399 | 0.169 | 0.144 | 0.420 | 0.251 | 0.187 | 0.388 | 0.440 | 0.315 |
| H | T85 | T86 | T87 | T88 | T89 | T90 | T91 | T92 | T93 | T94 | T95 | T96 |
| | 0.413 | 0.170 | 0.149 | 0.421 | 0.168 | 0.135 | 0.405 | 0.163 | 0.170 | 0.433 | 0.411 | 0.353 |

Micro-titre plate layout of phages and bacterial strains showing optical density values. Column 0 contains no phage. Columns 1–11 contain different phages. Row A contains the positive control strain (1043), sensitive to all the phages; row B contains growth medium only, rows C to E contain 3 replicates of strain 1; rows F to H contain 3 replicates of strain 13. Well A0 (control strain in the absence of phage) is used to obtain infection ratios.

TABLE 2

| | Phages | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| Strain 1 | 0.425 | 0.163 | 0.164 | 0.381 | 0.167 | 0.132 | 0.388 | 0.155 | 0.212 | 0.382 | 0.396 | 0.302 |
| | 0.417 | 0.16 | 0.168 | 0.399 | 0.169 | 0.144 | 0.42 | 0.251 | 0.187 | 0.388 | 0.44 | 0.315 |
| | 0.413 | 0.17 | 0.149 | 0.421 | 0.168 | 0.135 | 0.405 | 0.163 | 0.17 | 0.433 | 0.411 | 0.353 |
| Strain 1 median | 0.417 | 0.163 | 0.164 | 0.399 | 0.168 | 0.135 | 0.405 | 0.163 | 0.187 | 0.388 | 0.411 | 0.315 |
| Percentage growth | | 30.79 | 31.06 | 95.09 | 32.15 | 23.16 | 96.73 | 30.79 | 37.32 | 92.09 | 98.36 | 72.2 |
| Strain 2 | 0.227 | 0.219 | 0.216 | 0.246 | 0.217 | 0.239 | 0.237 | 0.055 | 0.053 | 0.262 | 0.228 | 0.209 |
| | 0.241 | 0.253 | 0.259 | 0.249 | 0.218 | 0.227 | 0.22 | 0.053 | 0.052 | 0.228 | 0.231 | 0.21 |
| | 0.258 | 0.268 | 0.235 | 0.275 | 0.237 | 0.218 | 0.227 | 0.055 | 0.052 | 0.226 | 0.219 | 0.225 |
| Strain 2 median | 0.241 | 0.253 | 0.235 | 0.249 | 0.218 | 0.227 | 0.227 | 0.055 | 0.052 | 0.228 | 0.228 | 0.21 |
| Percentage growth | | 106.28 | 96.85 | 104.18 | 87.95 | 92.67 | 92.67 | 2.61 | 1.04 | 93.19 | 93.19 | 83.76 |

Spreadsheet file. Column 0 contains no phage. Columns 1–11 contain different phages. Analysis of each strain (in this case strains 1 and 2) are carried out in triplicate. Within each strain the median of the three values is taken. The median is then used to calculate the percentage growth of phage wells (1–11) compared to the the control well (0).

TABLE 3

| Strain | Conventional Phage type | VT1/ VT2 | H type H7 | Source | Nature of source | Place of outbreak | Novel phage type | Notes |
|---|---|---|---|---|---|---|---|---|
| 322 | 2 | −/+ | + | H | O | WL | 2 | Fatality |
| 1563 | 2 | −/+ | + | H | O | CS | 2 | |
| 3487 | 2 | −/+ | + | H | S | | 2 | |
| 3932 | 2 | −/+ | + | H | S | | 2 | |
| 3964 | 2 | −/+ | + | H | S | | 2 | |
| 3969 | 2 | −/+ | + | H | S | | 1 only | |
| 3890 | 4 | −/+ | + | H | S | | 4 | |
| 3440 | 8 | +/+ | H− | H | O | F | 8 | Geriatric ward |
| 3486 | 8 | +/+ | H− | H | O | | 8 | Family — duplicate of 3454 |
| 1291 | 28 | −/+ | + | A | L | | 28 | Family outbreak. Animals also positive |
| 3602 | 28 | −/+ | + | H | O | Community | 1 only | Community — water-borne |
| 38952 | 28 | −/+ | + | H | S | | 28 | |
| 3936 | 28 | −/+ | + | H | S | | 28 | |
| 3946 | 28 | −/+ | + | A | S | | 1 only | |
| 3726 | 49 | −/+ | + | H | S | | 49 | |
| 3844 | 49 | −/+ | + | H | S | | 1 only | |
| 3970 | 49 | −/+ | + | H | S | | 49 | |
| 3694 | 54 | −/+ | + | A | S | | 54 | |
| 643 | RDNC | −/+ | + | A | L | — | 54 | Linked to case of human infection. Multiple isolates RDNC |
| 644 | RDNC | −/+ | + | A | L | — | 54 | Linked to case of human infection. Multiple isolates RDNC |
| 645 | RDNC | −/+ | + | A | L | — | 54 | Linked to case of human infection. Multiple isolates RDNC |
| 646 | RDNC | −/+ | + | A | L | — | 54 | Linked to case of human infection. Multiple isolates RDNC |
| 647 | RDNC | −/+ | + | A | L | — | 54 | Linked to case of human infection. Multiple isolates RDNC |
| 648 | RDNC | −/+ | + | A | L | — | 54 | Linked to case of human infection. Multiple isolates RDNC |
| 714 | RDNC | −/+ | + | H | S | — | 2 | |
| 785 | RDNC | −/+ | + | H | S | | 2 | Same zone pattern as 714 |
| 921 | RDNC | +/+ | + | H | S | | 1 only | Unique RDNC |
| 936 | RDNC | −/+ | + | H | S | | 1 only | |
| 3690 | RDNC | −/+ | + | A | S | | 1 only | |
| 3750 | RDNC | +/− | ? | A | S | | 1 only | only VT1+/VT2− |
| 530 0111 | Control | | | | | | Neg | |

*E. coli* O157 isolates together with their conventional phage type, verotoxin type, H antigen type, source [H = human, A = animal], nature of source [O = outbreak, S = sporadic, L = linked to human infection], place of outbreak [WL = West Lothian, CS = Central Scotland, F = Falkirk] and novel phage type.

What is claimed is:

1. An assay to identify bacteria, said assay comprising the following steps:

(a) providing an isolated colony of said bacteria;
   (b) combining said isolated colony of bacteria with a selected bacteriophage in a container, the combination of bacteria and phage being incubated in a medium containing the nutrients required for bacterial growth and which enables phage/bacteria interaction; and
   (c) determining the extent of bacterial growth compared to a control sample and analysing the value so obtained to predetermined growth data for known bacteria with said bacteriophage thereby identifying said bacteria.

2. An assay as claimed in claim 1 wherein the incubation medium is nutrient broth or Luria Bertani broth.

3. An assay as claimed in claim 1 wherein the extent of bacterial growth is determined by measuring the optical density of the sample.

4. An assay as claimed in claim 3 wherein the optical density is read using light of wavelength 590 nm to 630 nm.

5. An assay as claimed in claim 1 wherein the bacteria and phage are combined together in a well of a micro-titre plate.

6. An assay as claimed in claim 1 wherein the phage is pre-located in said container and retained therein by means of a fixant, by physical entrapment or by chemical interaction with the surface of the container.

7. An assay as claimed in claim 6 wherein said bacteria is retained by using 5% gelatin as fixant.

8. An assay to select a bacteriophage able to combat replication of a specific bacterial species, said assay comprising:

(a) providing an isolated colony of said bacteria;
   (b) combining said isolated colony of bacteria with a selected bacteriophage, said combination being held in a liquid medium containing the nutrients required for bacterial growth and incubating said combination;
   (c) determining the extent of bacterial growth; and
   (d) selecting any bacteriophage which has depressed the extent of bacterial growth compared to a control sample.

9. An assay as claimed in claim 8 wherein the incubation medium is nutrient broth or Luria Bertani broth.

10. An assay as claimed in claim 8 wherein the extent of bacterial growth is determined by measuring the optical density of the sample.

11. An assay as claimed in claim 10 wherein the optival density is read using light of wavelength 590 nm to 630 nm.

12. An assay as claimed in claim 8 wherein the bacteria and phage are combined together in a well of a micro-titre plate.

13. An assay as claimed in claim 8 wherein the phage is pre-located in said container and retained therein by means of a fixant, by physical entrapment or by chemical interaction with the surface of the container.

14. An assay as claimed in claim 13 wherein said bacteria is retained by using 5% gelatin as fixant.

15. An assay as claimed in claim 1 wherein said bacteria is separately incubated with up to 45 different phage subtypes.

16. An assay as claimed in claim 8 wherein said bacteria is separately incubated with up to 45 different phage subtypes.

* * * * *